United States Patent [19]

Wong

[11] 4,418,052
[45] Nov. 29, 1983

[54] NOVEL DIAGNOSTIC COMPOSITIONS AND METHOD FOR RADIOLOGIC IMAGING OF FIBRINOGEN DEPOSITION IN THE BODY

[76] Inventor: Dennis W. Wong, 2853 Sunnyglen Rd., Torrance, Calif. 90505

[21] Appl. No.: 177,503

[22] Filed: Aug. 12, 1980

[51] Int. Cl.$^3$ .................. A61K 43/00; A61K 49/00
[52] U.S. Cl. .................. 424/1.1; 260/112 B; 422/61; 424/9
[58] Field of Search .................. 424/1, 1.5, 9; 260/112 B; 422/61

[56] References Cited

U.S. PATENT DOCUMENTS 4,293,537 10/1981 Wong .................. 424/1

OTHER PUBLICATIONS

Wong et al., Int. J. Appl. Radilsotopes, vol. 29, No. 4–5, pp. 251–253, (May 1978).

Primary Examiner—Christine M. Nucker

[57] ABSTRACT

A novel injectable diagnostic composition comprises a fibrinolytic enzyme such as streptokinase-activated human plasmin or human urokinase, a stannous reducing agent and an alkaline sodium citrate reagent prepared and packaged as an instant non-radioactive labeling reagent kit to be used in conjunction with a source of $^{99m}$Tc-pertechnetate forming a radioactive tracer material suitable for use in scintigraphic imaging of fibrinogen or fibrin depositions in thromboembolic diseases, in myocardial infarction and in neoplasm.

15 Claims, No Drawings

DIAGNOSTIC COMPOSITIONS AND METHOD FOR RADIOLOGIC IMAGING OF FIBRINOGEN DEPOSITION IN THE BODY

BACKGROUND OF THE INVENTION

The leading cause of pulmonary and cerebral embolism is thrombophlebitis. Thromboembolism is caused by abnormalities of the blood vessel, the blood or the circulation resulting the formation of blood clots called thrombi. Within a short period of time, many of these blood clots become dislodged from the blood vessels and migrate freely as emboli via the circulation into the lung. These emboli are then trapped and cause serious complications interfering with normal circulation and gas exchange.

Formation of blood clots occurs frequently in myocardial infarction and neoplasm. Recent experimental findings have confirmed the existence of fibrin or clot deposits at the sites of infarcts and tumors. Due to microvascular damage or injury, the coagulation process is initiated in the early or acute phase of these diseases resulting in a well formed fibrin gel surrounding the injured tissue or tumors. The fibrin clot effectively cuts off blood supply to the area of infarction and further aggravates the patient's symptoms. In case of neoplasm, the invading tumor utilizes the fibrin gel as a protective shield against antibody activity from the host thus maintaining its rapid growth without hinderence.

Early diagnosis of thromboembolic diseases remains a considerable problem. Clinical diagnosis of venous thrombosis are neither specific nor reliable during the acute phase of thrombophlebitis and phlebography is an invasive, uncomfortable technique. Human fibrinogen labeled with the radionuclide $^{125}$I has been used for screening high risk or postoperative patients. Because of low energy gamma photon flux and necessarily limited doses of $^{125}$I, the use of radioiodinated fibrinogen is limited to surface monitoring technics. It is not a scintillation imaging agent. The screening procedure requires 7–10 days. Autologous human fibrinogen labeled with $^{123}$I or $^{131}$I has been advocated recently as thrombus imaging agents. These agents are still in early experimental stages and are not available for general medical use.

Attempts to localize and to detect thrombus using Technetium-99m labeled streptokinase, urokinase(Dugan, MA U.S. Pat. No. 3,812,245) and fibrinogen(Abramovici, et at, U.S. Pat. No. 4,057,617) have had little success. Since the optimal condition for preserving the physiobiological properties of proteins occurs within a narrow pH range of 7 to 7.4, proteins that are labeled with $^{99m}$Tc by the acidic method of Dugan(pH less than 2) or alkaline method of Abramovici(pH 11.6) are completely denatured. This renders protein substances labeled by their methods unsuitable for biological and medical applications. The existence of protein degradation products as described in their patents is further proof that proteins labeled at extremes of pH undergo drastic molecular alteration or transformation. Thus, these so called Tc-99m labeled proteins as claimed by Dugan and Abramovici do not have the same properties as they had prior to the labeling process. The use of denatured heterologous proteins in man carries risk of antigenic reaction and hepatitis transmission.

Protein denaturation and complete loss of biological activity are the primary concerns in the labeling of human plasma proteins with Tc-99m. To resolve these problems, the present inventor has developed a simple chemical method of labeling these protein substances with Tc-99m under physiological condition(Wong, DW, Patent pending, Ser. No. 939,820 filed Sept. 5, 1978 and now U.S. Pat. No. 4,293,537, and Wong, DW, et al, Int. J. Appl. Rad. and Isotopes 29:251, 1978). The basic labeling methodology involves the production of a $^{99m}$Tc(Sn)citrate complex species with high protein binding capacity at pH 7.4 prior to the addition of the protein. The actual labeling of the protein ligand with Tc-99m occurs at physiological conditions of pH, thus avoiding harsh treatment of the protein and preserving its biological properties. Experimental results have confirmed that plasma proteins such as figrinogen, antibodies or immunoglobulins, urokinase, thrombin and streptokinase-activated human plasmin labeled with Tc-99m by the present chemical process retain their natural physiological and immunological properties(Wong, DW, et al, J. Nucl. Med. 20:967, 1979).

Technetium-99m labeled plasma proteins which retain their natural biological properties after labeling are ideal scintillation imaging agents. Essentially, these radiolabeled protein substances will actively participate in the physiobiochemical processes in vivo in man or animals. Tc-99m autologous antibodies, for example, are immunologically active against specific antigens thus providing a simple, unique and highly specific means of detecting infectious lesions or tumors. Similarly, diseases such as venous and arterial thrombosis, pulmonary or cerebral embolism, myocardial infarction and tumors can be diagnosed using Tc-99m labeled antologous human fibrinogen, urokinase or streptokinase-activated human plasmin.

Technetium-99m labeled urokinase and streptokinase-activated human plasmin (plasmin-SK) offer additional advantages over Tc-99m or I-131 labeled fibrinogen. Among these are: (a) both fibrinolytic enzymes are safe and non-antigenic in man; (b) these enzymes are available commercially in pure form freed from possible hepatitis transmission; (c) they have been used clinically in patients for the treatment of thromboembolic diseases without serious side effects and (d) they are effective in localizing and detecting preformed or aged blood clots even at a latter stage of the disease.

SUMMARY OF THE INVENTION

A novel diagnostic composition comprises a fibrinolytic enzyme such as streptokinase-activated human plasmin or urokinase, a stannous reducing agent and an alkaline sodium citrate solution aseptically prepared in sealed, sterile non-pyrogenic containers and packaged as an instant non-radioactive labeling reagent kit. The said labeling kit is to be used in conjunction with a source of $^{99m}$Tc-pertechnetate forming an injectable radioactive tracer material suitable for use in scintigraphic imaging. In the process of preparing these labeled enzymes, a solution of $^{99m}$Tc-pertechnetate in normal saline is added to the lyophilized stannous chloride/0.05 N hydrochloric acid powder which when dissolved causes chemical reduction of Tc-99m. The reduced Tc-99m is treated with a pH 12.4 solution of sodium citrate/sodium hydroxide forming a protein binding $^{99m}$Tc(Sn)citrate complex species at pH 7.4. One milliliter of the reconstituted enzyme solution providing 5000 to 10,000 units of fibrinolytic activity is added to the radioactive admixture resulting in a stable $^{99m}$Tc-labeled urokinase or plasmin-SK ready for patient administration. Following intravenous injection, the radiolabeled enzyme will be adsorbed and bound to fibrin clots and increasing radioactivity should accumulate at the sites. This provides a simple and rapid means of localizing and detecting the presence of blod clots in thromboembolic diseases, in myocardial infarction and in neoplasm by scintillation imaging technics.

DETAILED DESCRIPTION OF THE INVENTION

This invention relates to Technetium-99m labeled protein substances useful for scintigraphic imaging of blood clots which are found in venous or arterial thrombosis, pulmonary or cerebral embolism, myocardial infarction and in neoplasm. The invention further relates to a packaged instant non-radioactive labeling reagent kit based on a physiologic chemical labeling process developed by the present inventor and a simple method of using said labeling kit with generally available $^{99m}$Tc-pertechnetate normal saline solution.

Basically, the labeling process requires the following sequential steps of: (1) initial reduction of $^{99m}$Tc-pertechnetate by a stannous reducing agent; (2) the formation of a protein binding $^{99m}$Tc(Sn)citrate complex species by the reaction of reduced $^{99m}$Tc in +4 or +5 valence state with a solution of sodium citrate; (3) raising the pH of the acidic radioactive admixture to 7.4 with sodium hydroxide(NaOH) solution; (4) covalent binding of the radionuclide $^{99m}$Tc to the protein ligand by the addition of a source of pure protein. Thus, in the present invention, the actual labeling of the protein with $^{99m}$Tc occurs at a pH 7.4 condition. The labeling yield is greater than 95% with less than 1% free or unbound $^{99m}$Tc. The radiolabeled product is ready for immediate use without any additional purification process. To facilitate the labeling process, the chemical reactions in steps 2 and 3 can be combined into a single step using an alkaline sodium citrate and NaOH solution.

Based on the chemical labeling process described above, an instant non-radioactive labeling reagent kit can be prepared in advance with individual components packaged separately in sealed, sterile non-pyrogenic containers. Such a labeling reagent kit is comprised of three basic components: (1) a sterile solution of stannous chloride dissolved in 0.05-0.1 N hydrochloric acid; (2) a 2% sodium citrate solution made alkaline to pH 12.4 with 1 N NaOH and (3) an aqueous solution of fibrinolytic enzyme such as plasmin-SK or urokinase providing from 5,000 to 20,000 units of fibrinolytic activity. All three reagents are aseptically prepared and sterilized by conventional means. The labeling reagent kit is to be used in conjunction with a source of $^{99m}$Tc-pertechnetate such as that generally eluted from a Technetium generator.

Any stannous salts such as stannous chloride(SnCl$_2$.2-H$_2$O), stannous fluoride (SnF) or stannous tartrate can be used for the chemical reduction of $^{99m}$Tc-pertechnetate. In the present embodiment, stannous chloride is preferred. The stannous reducing agent is prepared by dissolving the desired amount of stannous chloride in 0.05 N HCl solution. One-half to 1 ml of the reducing agent containing 0.1-5 mg of stannous chloride is packaged in a sealed, nitrogen-purged ampule or serum vial. Preferably, the stannous reducing agent is prepared and packaged in the form of a freeze-dried solid which aids in shipping and storage. The lyophilized solid mixture of stannous chloride and 0.05 N HCl can be reconstituted with $^{99m}$Tc-pertechnetate normal saline solution without loss of its reducing activity.

Alkaline sodium citrate solution is prepared by dissolving 2% W/V of trisodium citrate crystals is distilled water and adjusted to pH 12.4 with 1 N NaOH. One to 2 ml of this reagent is packaged in a sealed, sterile apyrogenic container. While it is preferred that an alkaline sodium citrate/NaOH solution be used to produce the $^{99m}$Tc(Sn)citrate complex species and to raise the pH to 7.4 condition prior to the addition of the protein, the same result can be achieved using two separate reagents, that is, a 2% sodium citrate solution and a 0.1-1 N NaOH solution. However, sodium citrate solution must be added first to react with the reduced $^{99m}$Tc prior to pH adjustment with NaOH. The amount of NaOH solution needed can be determined by a simple routine experiment by those skilled in the art. The alkaline sodium citrate/NaOH solution is stable when kept in refrigeration at 2°-8° C. To maintain a proper pH environment, it should be packaged in the form of a lyophilized solid. The lyophilized powder is reconstituted with 1-2 ml distilled water at time of use.

The amount of protein enzyme that can be labeled by the chemical method varies from 5000 to 50,000 units. Both plasmin-SK and urokinase are commercially available in relatively pure forms. Aliquots of these proteins in the amount of 10,000-20,000 units can be repackaged in sealed, sterile apyrogenic serum vials and to be reconstituted with pH 7.4 Sorenson's phosphate buffer just prior to labeling with $^{99m}$Tc. In the present invention, a concentration of 5000 to 10,000 units/ml diluent is adequate to bind up to 100 mCi of $^{99m}$Tc. Any pharmacologically acceptable diluents such as water for injection, normal saline, 5% dextrose in water having a neutral pH can be used to reconstitute or to dilute the protein to the desired concentration.

In use, the labeling reagent kit of the invention is mixed with a source of $^{99m}$Tc-pertechnetate in normal saline to form an efficiently labeled $^{99m}$Tc-plasmin-SK or $^{99m}$Tc-urokinase suitable for scintigraphic imaging of blood clots in thromboembolism, myocardial infarcts or neoplasm. The $^{99m}$Tc-labeled fibrinolytic enzyme of the invention is prepared and readied for injection in a simple three-steps procedure. In the first step, using an aseptic technique, 2-3 ml of $^{99m}$Tc-pertechnetate in normal saline solution providing 60-100 mCi of radioactivity is drawn into a syringe and is injected into the reaction vial containing the stannous reducing agent. Reduction of $^{99m}$Tc to a chemically active +4 or +5 valence state occurs when the lyophilized powder is dissolved by $^{99m}$Tc-pertechnetate normal saline solution. The content of the reaction vial is shaken for 1-10 minutes to allow complete reduction of the radionuclide. In the second step, a sufficient amount of reconstituted pH 12.4 sodium citrate/NaOH solution is added to the reduced $^{99m}$Tc solution to form the protein binding $^{99m}$Tc(Sn)citrate complex species and to produce a pH 7.4 condition prior to the addition of the enzyme. This generally ranges from 0.5 to 1 ml. In the third step, 1 ml of the reconstituted urokinase or plasmin-SK solution having 500-10,000 units of fibrinolytic activity is aseptically injected into the reaction vial containing the radioactive admixture resulting from step 2 and is allowed to incubate at 37° C. or at room temperature for 10-30 minutes. The resulting $^{99m}$Tc-labeled enzyme is stable for up to 48 hours without any evidence of radiochemical or biological decomposition. After incubation, the radioactive preparation is then intravenously injected into the patient.

The ability of plasmin-SK and urokinase to lyse arterial and venous thrombi has been well documented in animals and man. Although the exact mechanism of fibrinolysis or thrombolysis is unclear, it has been found that when these fibrinolytic enzymes in contact with a thrombus or an embolus, they are readily adsorbed on to the surface of the blood clots and effect thrombolysis through contact. Recent investigation has confirmed that radiolabeled enzymes such as $^{125}$I-plasminogen and $^{125}$I-plasmin are strongly bound to the fibrin molecules in the fibrin clot. The amount of radioactive enzyme bond to the fibrin clot is determined by the size and the aged of blood clot. A well-formed or preformed clot such as those found in embolism, infarcts or tumors will cumulate more fibrinolytic enzymes than a newly formed clot found in acute phase of thrombophlebitis. Technetium-99m labeled plasmin-SK or urokinase will provide a simple and unique means of detecting these abnormalites by scintigraphic imaging technics. Following an intravenous administration of a dose of the radioactive tracer, whole body scans are taken at various time intervals, e.g. 0.5–24 hours, with a rectilinear scanner or an Anger scintillation camera. Increased radioactivity at the sites of these lesions indicates the presence of thrombi, emboli, infarcts or tumors.

The following examples illustrate the labeling procedure for preparing $^{99m}$Tc-labeled fibrinolytic enzymes such as plasmin-SK or urokinase:

EXAMPLE I

Procedure for labeling fibrinolytic enzymes with $^{99m}$Tc

1. Inject 2 to 3 ml (60–100 mCi) of $^{99m}$Tc-pertechnetate normal saline solution into a sterile evacuated serum vial containing 0.5 ml of a solution of 0.1 mg stannous chloride in 0.05 N HCl. Mix the contend of the reaction vial vigorously for 1–10 minutes to allow complete reduction of $^{99m}$Tc-pertechnetate.
2. Raise the pH of the mixture of step (1) to 7.4 by adding 0.5–1 ml 2% sodium citrate solution previously adjusted to pH 12.4 with 1 N NaOH.
3. Immediately inject 1 ml(5,000–10,000 units) plasmin-SK or urokinase solution into the reaction vial containing the admixture from step (2) slowly with gentle swirling.
4. Incubate the contents of the reaction vial at room temperature for 10–30 minutes. The fibrinolytic enzyme is firmly labeled and ready for use without additional purification steps.
5. Perform complete qualitative and quantitative radiochemical analyses. The final concentration should be in the range of 15–25 mCi $^{99m}$Tc-labeled plasmin-SK or urokinase/ml.
6. For scintigraphic imaging, a dose of 3–25 mCi $^{99m}$Tc-plasmin-SK or $^{99m}$Tc-urokinase is sufficient to detect the presence of fibrinogen or fibrin clot in throboembolic diseases, in myocardial infarcts and in tumors by scanning the patient with a rectilinear scanner or an Anger scintillation camera and by observing areas of increased radioactivity at the sites of these lesions as seen in the scans.

EXAMPLE II

Formulation of the non-radioactive labeling reagent kit for preparing $^{99m}$Tc-labeled plasmin-SK or $^{99m}$Tc-labeled urokinase Essentially, the labeling reagent kit consists of three basic components each aseptically prepared and packaged separately in sterile non-pyrogenic serum vials. When properly prepared, lyophilized and stored at 2°–8° C., the labeling reagent kit is stable for more than two years.

Vial #1. Stannous reducing reagent. Each vial contains 0.1–5 mg of stannous chloride dissolved in 0.05 N HCl solution. The content of the vial is lyophilized and stored under nitrogen.

Vial #2. Citrate complexing reagent. Each vial contains 1–2 ml of an aqueous solution of 2% sodium citrate made alkaline to pH 12.4 with 1 N NaOH solution. The content of the vial is lyophilized and stored under nitrogen. This reagent is to be reconstituted with 1–2 ml Water for Injection, U.S.P. at time of use.

Vial #3. Fibrinolytic enzyme. Each vial contains 10,000–20,000 units of plasmin-SK or urokinase in lyophilized powder form and properly preserved with any pharmaceutically acceptable preservatives and stabilizing agents.

EXAMPLE III

Procedure for preparing $^{99m}$Tc-plasmin-SK or $^{99m}$Tc-urokinase injection utilizing the labeling reagent kit The directions outlined below must be carefully followed for optimum preparation of $^{99m}$Tc-labeled fibrinolytic enzyme injections:

1. Remove the kit from the refrigerator and warm to room temperature before continuing.
2. Reconstitute the citrate complexing reagent of vial #2 with 1–2 ml of Water for Injection, U.S.P. until completely dissolved.
3. Reconstitute the content of vial #3 which contains the fibrinolytic enzyme plasmin-SK or urokinase with Water for Injection, U.S.P. or normal saline to a concentration of 5,000–10,000 units/ml.
4. Aseptically inject 2 ml $^{99m}$Tc-pertechnetate normal saline solution providing up to 100 mCi of radioactivity into the reaction vial #1 containing the stannous reducing reagent and withdraw an equal volume of air.
5. Shake the contents of vial #1 vigorously for 1 minute and incubate at room temperature for additional 5–10 minutes to allow complete reduction of $^{99m}$Tc.
6. Inject 0.5–1 ml of the reconstituted pH 12.4 citrate complexing reagent of vial #2 into the reaction vial #1 to bring the pH of the admixture of 7.4.
7. Immediately, inject 1 ml of the reconstituted fibrinolytic enzyme solution into the reaction vial #1 slowly with gentle swirling.
8. Incubate the contents of vial #1 at room temperature for 10–30 minutes after mixing to allow maximum labeling.
9. Do not use the preparation after 8 hours from time of formulation.

The above examples and the described procedures are for illustrative purposes only and are not intended to be limiting of the scope of the invention. It will be apparent to those skilled in the art that both may be modified within the scope of the invention defined in the following claims.

I claim:

1. A method of labeling human or animal fibrinolytic enzymes with the rationuclide Technetium-99m at physiological pH 6–8 condition comprising the sequential steps of:
   a. treating 2–3 ml(60–100 mCi) $^{99m}$Tc-pertechnetate in normal saline with 0.5 ml of a solution of 0.1–5 mg stannous chloride, stannous tartrate or stannous fluoride in 0.05 N hydrochloric acid at room temperature for about 1–10 minutes;
   b. raising the pH of the acidic mixture of step (a) to 7.4 with a sufficient amount of pH 12.4 sodium citrate/NaOH solution;
   c. adding 5,000 to 10,000 units of the desired fibrinolytic enzyme to be labeled in 1–2 ml diluents to the admixture of step (b) and incubating at 37° C. or at room temperature for 10–30 minutes.

2. Streptokinase-activated human plasmin selected from a group of fibrinolytic enzyme labeled with $^{99m}$Tc accoding to the method of claim 1.

3. Human urokinase selected from a group of fibrinolytic enzyme labeled with $^{99m}$Tc according to the method of claim 1.

4. A method of detecting fibrinogen or fibrin clot deposition in thromboembolic diseases, myocardial infarction or tumors in a mammal comprising:
   a. intravenously administering to the mammal 0.1–25 mCi of $^{99m}$Tc-streptokinase activated human plasmin of claim 2;
   b. scanning said mammal with a conventional scintillation camera or a rectilinear scanner at various time intervals from 0.5–24 hours;
   c. observing increasing radioactivity cumulated at the sites of these lesions as seen in the scintigraphic scans.

5. A method of detecting fibrinogen or fibrin clot deposition in thromboembolic diseases, myocardial infarction or tumors in a mammal comprising;
   a. intravenously administering to the mammal 0.1–25 mCi of $^{99m}$Tc-human urokinase of claim 3;
   b. scanning said mammal with a conventional scintillation camera or a rectilinear scanner at various time intervals from 0.5–24 hours;
   c. observing increasing radioactivity cumulated at the sites of these lesions as seen in the scintigraphic scans.

6. A kit for labeling fibrinolytic enzymes with $^{99m}$Tc-pertechnetate at physiological pH comprising a stannous reducing agent, a citrate complexing agent and a solution of fibrinolytic enzyme aseptically prepared and packaged separately in sealed, sterile, apyrogenic containers, wherein said kit is used with a solution of $^{99m}$Tc-pertechnetate in normal saline.

7. A kit according to claim 6, wherein said stannous reducing agent is stannous ions selected from the group consisting stannous chloride, stannous fluroride or stannous tartrate.

8. A kit according to claim 7, wherein said stannous reducing agent is dissolved in 0.05 to 0.1 N HCl in the amount of 0.1–5 mg per ml.

9. A kit according to claim 8, wherein said stannous reducing agent is present in the amount of 0.2–0.5 mg per ml of 0.05 N HCl solution and packaged in the form of a freeze-dried solid.

10. A kit according to claim 6, wherein said citrate complexing agent is an aqueous solution of 0.5–10% sodium citrate made alkaline to a pH above 8 with 1 N NaOH.

11. A kit according to claim 6, wherein said fibrinolytic enzyme is selected from the group consisting streptokinase-activated human plasmin or human urokinase.

12. A kit according to claim 11, wherein said fibrinolytic enzyme is present in the amount of 5,000 to 50,000 units dissolved in an aqueous medium together with any pharmaceutically acceptable preservatives or stabilizers.

13. A kit according to claim 12, wherein said fibrinolytic enzyme solution is packaged in the form of a freeze-dried solid.

14. A kit according to claim 10, wherein 1–5 ml of an aqueous solution of 2% sodium citrate at pH 12.4 is packaged in the form of a freeze-dried solid as said citrate complexing agent.

15. A method of preparing $^{99m}$Tc-labeled fibrinolytic enzyme at physiological pH suitable for use in radiologic imaging comprises the sequential steps of:
   a. reconstituting the citrate complexing agent with 1–5 ml Water for Injection until completely dissolved;
   b. redissolving the fibrinolytic enzyme with normal saline, Water for Injection or any pharmaceutically acceptable carrier to a concentration of 5,000–10,000 units per ml;
   c. dissolving the freeze-dried stannous reducing agent with 2–3 ml (60–100 mCi) $^{99m}$Tc-pertechnetate in normal saline for about 1–10 minutes;
   d. reacting the mixture of step (c) with 0.5–1 ml of the alkaline citrate complexing solution to a pH 7.4 condition;
   e. adding to the admixture of step (d) 1 ml(5,000–10,000 units) of the reconstituted fibrinolytic enzyme solution and incubating the contents at 37° C. or at room temperature for 10–30 minutes.

* * * * *